United States Patent [19]

Tomcufcik et al.

[11] 4,261,892

[45] Apr. 14, 1981

[54] 2,4,6-TRIS-(SUBSTITUTED-AMINO)-S-TRIAZINES

[75] Inventors: Andrew S. Tomcufcik, Old Tappan, N.J.; Adolph E. Sloboda, New City, N.Y.

[73] Assignee: American Cyanamid Company, Stamford, Conn.

[21] Appl. No.: 17,796

[22] Filed: Mar. 5, 1979

Related U.S. Application Data

[63] Continuation-in-part of Ser. No. 895,572, Apr. 12, 1978, abandoned.

[51] Int. Cl.³ .................. C07D 451/14; C07D 451/06; C07D 403/14; C07D 403/12
[52] U.S. Cl. .................. 260/243.3; 544/113; 544/61; 544/197; 544/198

[58] Field of Search ............... 544/198, 197, 207, 113, 544/61; 260/243.3

[56] References Cited

U.S. PATENT DOCUMENTS

| | | | |
|---|---|---|---|
| 3,577,417 | 5/1971 | Cantrall et al. | 544/197 |
| 3,706,741 | 12/1972 | Papaioannou | 544/197 |

*Primary Examiner*—John M. Ford
*Attorney, Agent, or Firm*—Edward A. Conroy, Jr.

[57] ABSTRACT

This disclosure describes new compounds and compositions of matter useful as anti-inflammatory agents and as inhibitors of the progressive joint deterioration characteristic of arthritic disease and the methods of meliorating inflammation and of inhibiting joint deterioration in mammals therewith, the active ingredients of said compositions of matter being certain 2,4,6-tris(substituted-amino)-s-triazines.

11 Claims, No Drawings

2,4,6-TRIS-(SUBSTITUTED-AMINO)-S-TRIAZINES

CROSS REFERENCE TO RELATED APPLICATION

This application is a continuation-in-part of our co-pending application Ser. No. 895,572, filed Apr. 12, 1978, now abandoned.

BRIEF SUMMARY OF THE INVENTION

This invention relates to new organic compounds and, more particularly, is concerned with novel $N^2,N^4,N^6$-tris(substituted)-melamines which may be represented by the following structural formula:

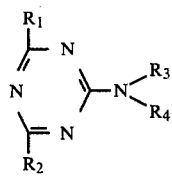
(I)

wherein $R_1$ is alkylamino having from 4 to 8 carbon atoms inclusive, 1-adamantylamino, 2-adamantylamino, exo[2.2.1]-norbornylamino, endo[2.2.1]norbornylamino, 3-azabicyclo[3.2.1]-octyl, 1,8,8-trimethyl-3-azabicyclo[3.2.1]octyl, 3-azabicyclo-[3.3.1]nonyl, 9-azabicyclo[3.3.1]nonyl, 2-azabicyclo[3.2.2]nonyl, 3-azabicyclo[3.2.2]nonyl or endo-3-hydroxy-8-azabicyclo[3.2.1]-oct-8-yl; $R_2$ is 3-azabicyclo[3.2.1]-octyl, 1,8,8-trimethyl-3-azabicyclo[3.2.1]octyl, 3-azabicyclo[3.3.1]nonyl, 9-azabicyclo[3.3.1]nonyl, 2-azabicyclo[3.2.2]nonyl, 3-azabicyclo[3.2.2]nonyl or endo-3-hydroxy-8-azabicyclo[3.2.1]oct-8-yl; $R_3$ is hydrogen or alkyl having up to 4 carbon atoms; $R_4$ is 2-(2-pyridyl)ethyl, alkyl having from 4 to 8 carbon atoms, inclusive, phenyl, monohalo (F, Cl, Br)phenyl, 1-adamantyl, 2-adamantyl, exo[2.2.1]norbornyl, endo[2.2.1]norbornyl or a monovalent moiety of the formula:

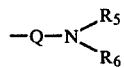

wherein Q is a divalent moiety selected from the group consisting of those of the formulae:

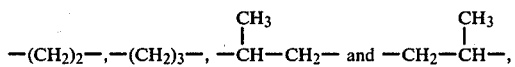

$R_5$ is alkyl having up to 4 carbon atoms, $R_6$ is alkyl having up to 4 carbon atoms, and $R_5$ and $R_6$ taken together with their associated N(itrogen) is piperidino, morpholino, pyrrolidino or thiomorpholino with the proviso that when $R_4$ is alkyl, adamantyl or norbornyl then $R_3$ must be hydrogen; and $R_3$ and $R_4$ taken together with their associated N(itrogen) is 3-azabicyclo[3.2.-1]octyl, 1,8,8-trimethyl-3-azabicyclo[3.2.1]octyl, 3-azabicyclo[3.3.1]nonyl, 9-azabicyclo[3.3.1]nonyl, 2-azabicyclo[3.2.2]nonyl, 3-azabicyclo[3.2.2]nonyl, endo-3-hydroxy-8-azabicyclo[3.2.1]oct-8-yl, pyrrolidino, piperidino, hexamethyleneimino, heptamethyleneimino or a monovalent moiety of the formula:

wherein R is hydrogen, alkyl having up to 4 carbon atoms, phenyl, p-methoxyphenyl or carboalkoxy having up to 4 carbon atoms.

DETAILED DESCRIPTION OF THE INVENTION

The novel compounds of the present invention are obtainable as crystalline materials having characteristic melting points and absorption spectra. They are appreciably soluble in many organic solvents such as lower alkanols, acetone, ethyl acetate, and the like, but are generally insoluble in water. These compounds are capable of forming acid-addition and quaternary ammonium salts with a variety of organic and inorganic salt-forming reagents when the substituent —$NR_3R_4$ contains a basic nitrogen atom. Thus, acid-addition salts, formed by admixture of the organic free base with an equivalent of an acid, suitably in a neutral solvent, are formed with such acids as sulfuric, phosphoric, hydrochloric, hydrobromic, citric, tartaric, acetic, and related acids. In like manner, quaternary ammonium salts may be formed by reaction of the free bases with an equivalent of a variety of organic esters of sulfuric, hydrohalic and aromatic sulfonic acids. The organic reagents employed for quaternary ammonium salt formation are preferably lower alkyl halides. The acid-addition and quaternary ammonium salts of the novel compounds of the present invention are, in general, crystalline solids relatively soluble in water, methanol and ethanol but relatively insoluble in non-polar organic solvents such as diethyl ether, benzene, toluene, and the like. For purposes of this invention, the free bases are equivalent to their non-toxic acid-addition and quaternary ammonium salts.

The novel compounds of the present invention have been found to be highly useful for meliorating inflammation and associated joint deterioration in mammals when administered in amounts ranging from about one milligram to about 250 mg. per kilogram of body weight per day. A preferred dosage regimen for optimum results would be from about 5 mg. to about 100 mg. per kilogram of body weight per day, and such dosage units are employed that a total of from about 0.35 gm. to about 7.0 gm. of the active ingredient for a subject of about 70 kg. of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. A decided practical advantage of this invention is that the active ingredient may be administered in any convenient manner such as by the oral, intravenous, intramuscular, topical, or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of active compound dissolved in the above vehicle may vary from 0.10% to 10.0% by weight, it is preferred that the amount of active compound employed be from about 3.0% to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, phenyl mercuric nitrate, benzalkonium chloride, phenethyl alcohol, p-chlorophenyl-α-glycerol ether, methyl and propyl parabens, and thimerosal. As a practical matter it is also convenient to employ antioxidants. Suitable antioxidants include, for example, sodium bisulfite, sodium metabisulfite, and sodium formaldehyde sulfoxylate. Generally, from about 0.05% to about 0.2% concentrations of antioxidant are employed.

For intramuscular injection, the preferred concentration of active compound is 0.25 to 0.50 mg./ml. of the finished compositions. These active compounds are equally adapted to intravenous administration when diluted with water or diluents employed in intravenous therapy such as isotonic glucose in appropriate quantities. For intravenous use, initial concentrations down to about 0.05 to 0.25 mg./ml. of active compound are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of the unit. The amount of active ingredient in such therapeutically useful compositions is such that a suitable dosage will be obtained. Preferred compositions or preparations according to the present invention are prepared so that an oral dosage unit form contains between about 50 and 250 milligrams of active compound.

The tablets, troches, pills, capsules and the like may also contain the following: a binder such a gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

Adjuvant-induced experimental polyarthritis is a specific systemic disease of the rat which shares interesting similarities with rheumatoid arthritis. Specifically, the histology of the two diseases bears a remarkable resemblance as shown by C. M. Pearson et al., Am. J. Pathol. 42, 73 (1963). E. M. Glenn, Am. J. Vet. Res. 27 (116), 339 (1966) has classified adjuvant-induced polyarthritis as a crippling and permanent deformity resulting from diffuse connective tissue involvement around certain susceptible joints in the rat. Zahiri et al., Can. Med. Ass. J. 101, 269 (1969) have shown that the fusiform swelling of the distal joints is associated with edema, congestion and synovitis including pannus formation, all of which precede the ultimate destruction of bone and cartilage. Furthermore, Zahiri et al. indicate that the cartilage destruction in the joint is due to an invasive pannus which originates in the marginal synovium and extends across the articular surface to erode it. When non-steroidal, anti-inflammatory agents such as indomethacin inhibit arthritic paw swelling, which is composed of inflammatory cell infiltrates, they have also been shown to prevent joint and bone deterioration. See S. Wong et al., J. Pharm. & Exptl. Ther. 185, 127 (1973) and G. R. Bobalick et al., Agents & Actions 4, 364 (1974). The most pertinent reference showing the relationship between arthritis and joint deterioration is an X-ray analysis of adjuvant arthritis in the rat by Blackham et al., Agents & Actions 7, 145 (1977). In a similar manner, inhibition of the progress or arthritis in paws of rats treated with the compounds of this invention also lessens associated joint deterioration.

The following test shows the activity of the compounds of this invention against chronic inflammation in adjuvant-induced arthritis which is accompanied by joint destruction. Groups of three Royal Hart, Wistar strain rats weighing 200±10 grams each were injected intradermally in the right hind paw with Freund's adjuvant (dried human tubercle bacilli in a mineral oil vehicle) at a dose of 2 mg./kg. of body weight. Test compounds were administered orally in a 1.5% starch vehicle at various doses once daily on days 0 through 13 post challenge. Control rats were treated in a similar manner, but given only starch vehicle. On the 14th and 21st day post challenge the diameter of the injected paw (primary lesion) was measured by micrometer caliper. The volume of inflamed paws were estimated from these measurements and the results are expressed as percent inhibition of swelling as compared to controls. At the same time, the other inflamed sites, such as ears, paws and tail (secondary lesions) were observed and each rat was graded as to degree of inflammation and swelling present. The grading is based on a scale of 0 to 24 where 0 represents a complete absence of induced arthritic nodules and 24 represents the maximum degree of inflammation. The mean grade for each treated group is calculated and the effects of each compound are expressed as percent inhibition of the control grade. Table I below records the results of tests conducted with the compounds of this invention and known anti-inflammatory agents. The compounds of this invention appear to suppress the progression of the arthritis and associated joint deterioration.

TABLE I

The Effect of Anti-Inflammatory Agents on Adjuvant Arthritis In Rats

| Compound | Oral Dose mg./kg. of Body Wgt. | Dead/Treated at 21 Days | Mean Weight Gain (grams) | | % Inhibition of Swelling (primary lesion) | | % Inhibition of Control Grade (secondary lesion) | |
|---|---|---|---|---|---|---|---|---|
| | | | Day 14 | Day 21 | Day 14 | Day 21 | Day 14 | Day 21 |
| Normal rats | — | 8/186 | 77 | 112 | — | — | — | — |
| Adjuvant Controls | — | 56/630 | 36 | 31 | 0 | 0 | 0 | 0 |
| 3-{4,6-bis[(1,1,2,2-tetramethylpropyl)-amino]-s-triazin-2-yl}-3-azabicyclo[3.2.2]-nonane | 100 | 1/18 | 73 | 62 | 74 | 41 | 69 | 45 |
| | 50 | 0/36 | 56 | 58 | 58 | 34 | 48 | 20 |
| | 25 | 1/18 | 74 | 70 | 42 | 24 | 44 | 12 |
| 3-[4,6-bis(1,1,3,3-tetramethylbutylamino)-s-triazin-2-yl]-3-azabicyclo[3.2.2]nonane | 50 | 2/18 | 76 | 67 | 59 | 23 | — | — |
| Indomethacin | 2 | 8/57 | 68 | 68 | 51 | 24 | 38 | 25 |
| | 1 | 9/54 | 63 | 65 | 46 | 19 | 34 | 20 |
| | 0.5 | 5/54 | 53 | 51 | 40 | 20 | 25 | 17 |
| | 0.25 | 0/9 | 51 | 57 | 30 | 4 | 22 | 4 |
| Aspirin | 400 | 18/57 | 41 | 55 | 73 | 48 | 58 | 45 |
| | 200 | 10/66 | 40 | 44 | 48 | 27 | 26 | 17 |
| | 100 | 18/63 | 48 | 53 | 36 | 13 | 19 | 8 |
| | 50 | 2/21 | 56 | 44 | 23 | 3 | 12 | 9 |
| Phenylbutazone | 150 | 2/27 | 40 | 50 | 75 | 44 | 54 | 31 |
| | 75 | 2/39 | 51 | 50 | 62 | 28 | 27 | 15 |
| | 37.5 | 5/39 | 53 | 53 | 56 | 14 | 18 | 13 |
| | 18.8 | 2/21 | 50 | 45 | 31 | 7 | 4 | 8 |
| 2-(tert-butylamino)-4-(1,1,3,3-tetramethyl-butylamino)-6-(3-azabi-cyclo[3.2.2]nonyl)-s-triazine | 50 | 3/18 | 85 | 87 | 42 | 14 | — | — |
| 3-[4,6-bis(tert-butyl-amino)-s-triazin-2-yl]--3-azabicyclo[3.2.2]nonane | 50 | 1/9 | 87 | 69 | 61 | 22 | — | — |
| 2-(n-butylamino)-4,6-bis(3-azabicyclo[3.2.2]-nonyl)-s-triazine | 50 | 2/12 | 82 | 107 | 46 | 32 | — | — |
| 2-(p-fluoroanilino)-4-(1,1,3,3-tetramethyl-butylamino)-6-(3-azabi-cyclo[3.2.2]nonyl)-s-triazine | 50 | 1/18 | 68 | 50 | 32 | 18 | — | — |
| 2-(1,1,2,2-tetramethyl-propylamino)-4-(1,1,3,3-tetramethylbutylamino)-6-(3-azabicyclo[3.2.2]-nonyl)-s-triazine | 50 | 0/12 | 66 | 91 | 74 | 42 | — | — |
| $N^2$-(1-adamantyl)-$N^4,N^6$-bis(1,1,2,2-tetramethyl-propyl)melamine | 50 | 1/12 | 94 | 89 | 47 | 17 | — | — |
| $N^2$(2-adamantyl)-$N^4,N^6$-bis(1,1,2,2-tetramethyl-propyl)melamine | 50 | 1/3 | 148 | 181 | 79 | 83 | — | — |
| $N^2$-(exo[2.2.1]norbornyl)-$N^4,N^6$-bis(1,1,2,2-tetra-methylpropyl)melamine | 50 | 0/3 | 97 | 93 | 49 | 24 | — | — |

The novel $N^2,N^4,N^6$-tris(substituted)melamines of the present invention may be readily prepared (1) by reacting a compound of the formula:

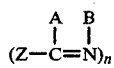

wherein n=1, 2 or 3; Z is the same or different and Z is chloro, bromo, fluoro, iodo, —O-alkyl, —O-phenyl, —S-alkyl, —$N_3$, —CN, —$N^+(CH_3)_3$, —$NH_2$, trichloromethyl, trifluoromethyl, —$R_1$, —$R_2$ or —$NR_3R_4$ wherein $R_1$, $R_2$, $R_3$ and $R_4$ are as hereinabove defined; A and B are chemical valencies which, when taken together form a single bond, or may be bonded to other atoms in a symmetrically or unsymmetrically substituted dimeric or trimeric open chain or a symmetrically or unsymmetrically substituted s-triazine ring;

(2) with compounds of the formulae:

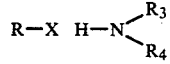

wherein $R_3$ and $R_4$ are as hereinabove defined; R is alkyl having from 4 to 8 carbon atoms, 1-adamantyl, 2-adamantyl, exo[2.2.1]-norbornyl or endo[2.2.1]norbornyl; X is —$NH_2$,

—CHO, —NHY (wherein Y is —CN, —NH$_2$, —OH, acyl or sulfonyl), —Cl, —Br, —OH, —N$^+$(CH$_3$)$_3$, or —NHR wherein R is as defined above; and wherein when Y and R are taken together with the nitrogen atom to which they are attached form a polymethyleneimino ring of from 4 to 6 carbon atoms and contain from zero to 4 methyl groups; and with the proviso that when X is the same group as Z, then X and Z can only be —NH$_2$, —NHR or —NR$_3$R$_4$ wherein R, R$_3$ and R$_4$ are as defined above;

(3) in the presence or absence of a Lewis acid catalyst in a stepwise manner when the substituents on the s-triazine product are different, or stepwise and/or concurrently when the substituents on the s-triazine are the same;

(4) and when X is

or —CHO, the resultant compound is reduced to give a compound of Formula (I);

(5) and when the resultant compound is in the monomeric form RNH—C≡N, it is trimerized to the tris(substituted-amino)-s-triazine by heat treatment with alkali;

(6) and when the resultant compound is in the form of an isomelamine it may be isomerized into an s-triazine of Formula (I) by treatment with a base.

Thus, this invention provides a process for producing a compound of Formula (I) and the pharmaceutically acceptable acid-addition salts thereof wherein R$_1$, R$_2$, R$_3$ and R$_4$ are as hereinabove defined by reacting a compound of the formula:

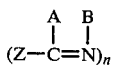

wherein n=3 and A and B are bonds in a 6 membered ring, specifically:

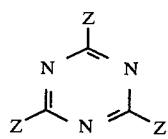

wherein Z is as defined above with compounds of the formulae:

R—X

H—NR$_3$R$_4$ wherein R, R$_3$, R$_4$ and X are as defined above, in the presence or absence of a Lewis acid catalyst in a stepwise manner using different amines when the final amino substituents on the s-triazine product are different, or in a stepwise in situ or concurrent manner when these substituents on the product are the same.

The present invention also provides a process for preparing compounds of the formula:

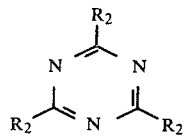

and the pharmaceutically acceptable acid-addition salts thereof wherein R$_2$ is as hereinabove defined by reacting a compound of the formula:

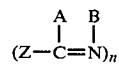

wherein n=1 and A and B together form a chemical bond, specifically,

wherein Z is as defined above, with a compound of the formula:

R$_2$—H wherein R$_2$ is as hereinabove defined and the resultant monomeric compound R$_2$—C≡N trimerized to the

structure, namely,

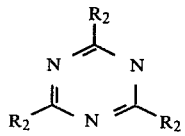

by heat treatment with alkali whereby any trimer in the isomelamine form is rearranged to the malamine structure above in the course of this heat treatment with alkali.

The present invention also provides a process for preparing compounds of Formula (I) and the pharmaceutically acceptable acid-addition salts thereof by reacting a compound of the formula:

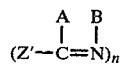

wherein n=3 and A and B are bonds in a 6-membered ring, specifically:

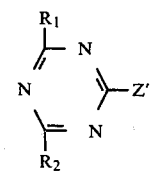

wherein Z' is chloro, bromo, iodo, fluoro, trihalomethyl, trimethylammonio or -O-phenyl with a compound of the formula:

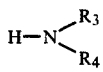

wherein $R_1$, $R_2$, $R_3$ and $R_4$ are as defined above, in the presence or absence of a Lewis acid catalyst in a stepwise manner using different amines when the final amino substituents on the s-triazine product are different, or in a stepwise in situ or concurrent manner when these substituents on the product are the same.

The present invention also provides a process for preparing compounds of Formula (I) and the pharmaceutically acceptable acid-addition salts thereof by reacting a compound of the formula:

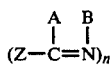

wherein $n=3$ and A and B are bonds in a 6-membered ring, specifically,

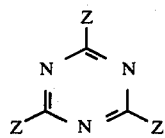

wherein Z is chloro, bromo, iodo, fluoro, trihalomethyl, trimethylammonio, or -O-phenyl with amines of the formulae:

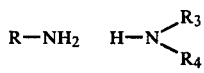

wherein R, $R_3$ and $R_4$ are as hereinbefore defined in the presence or absence of a Lewis acid catalyst in a stepwise manner using different amines when the final amino substituents on the s-triazine product are different, or in a stepwise in situ or concurrent manner when these substituents on the product are the same.

A general reaction scheme for preparing the compounds of the present invention is illustrated below.

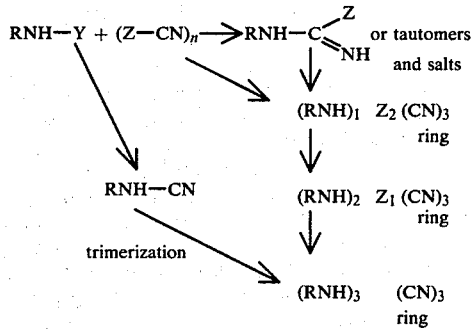

wherein n, R, Y and Z are as defined above. As indicated by the above scheme, the products of the invention may be formed in a stepwise manner when the substituents are different or may be formed in a stepwise and/or concurrent manner when the substituents are symmetrical. By "stepwise" is meant that the intermediates (the mono- and di-aminated s-triazines) may be isolated from the reaction mixture and subsequently reacted with another reagent, ultimately obtaining the product of this invention. By "concurrent" is meant that the reactants are mixed together in the same reaction vessel and the intermediate products are not isolated during the course of the reaction.

It should be noted that the reactivities of the starting materials and/or intermediates decreases in the following order: non-animated > mono-aminated > di-aminated and more vigorous reaction conditions are needed when a greater number of amino groups are present. Illustrating the above reaction scheme in more detail and using an s-triazine bearing three displaceable groups as an example:

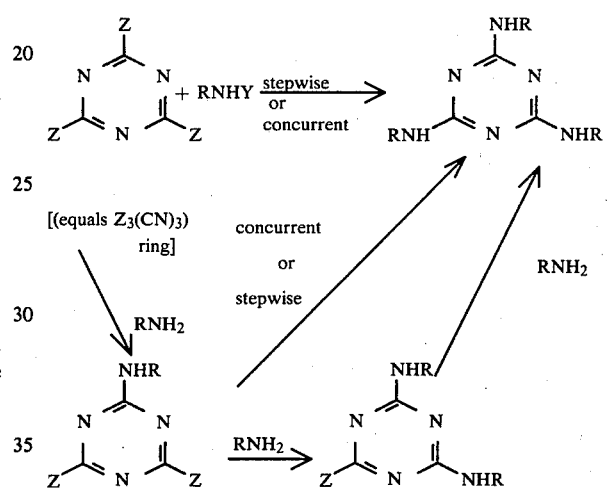

The reaction may also be conducted in the presence of a Lewis acid catalyst, for example, $H^+$, $F_3CCOOH$, 2-pyridone and $Sb(Hal)_5$.

The products resulting from the trimerization of a substituted cyanamide may be partly in the form of an isomelamine with substituents at one or more ring nitrogens which may then be isomerized to the compounds of the present invention by treating the isomelamine with base, e.g.,

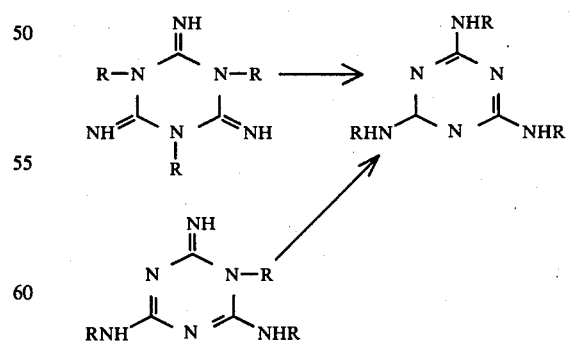

A preferred embodiment for the preparation of the 2,4,6-tris(alkylamino)-s-triazines of the present invention is by the process of reacting cyanuric chloride and an appropriate amine in accordance with the following reaction scheme:

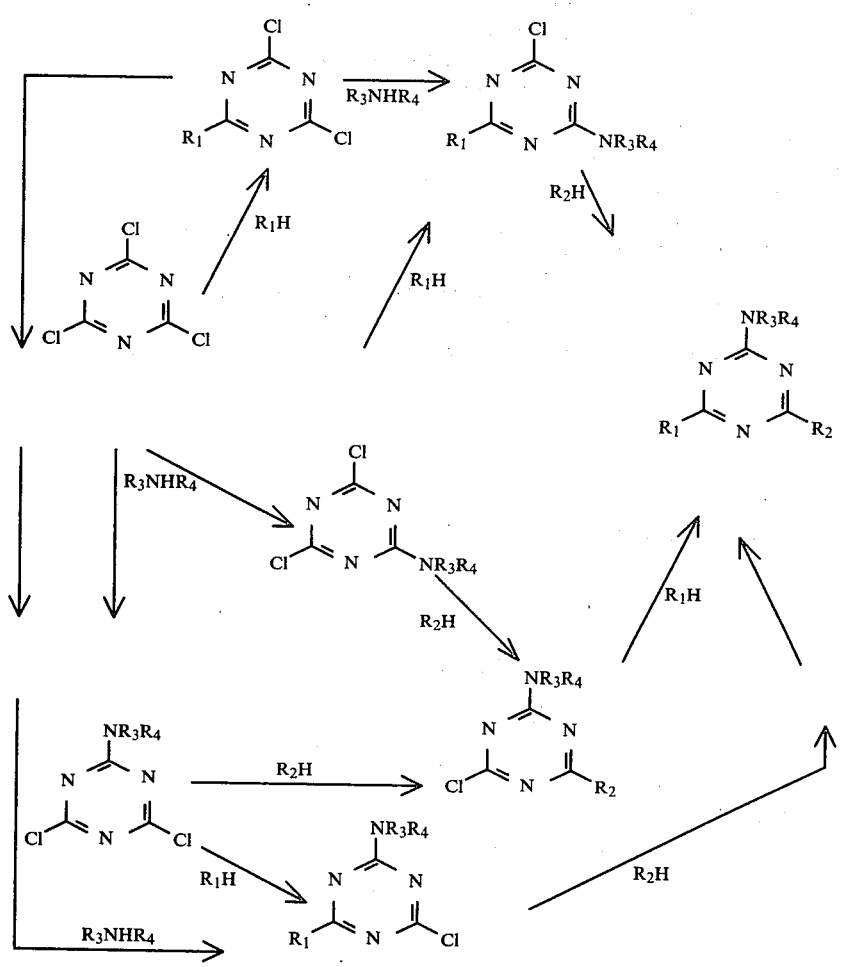

Each path above proceeds in a stepwise manner when preparing the unsymmetrically and symmetrically-substituted s-triazines of the invention (that is, wherein the radicals $R_1$-, $R_2$- and $R_3R_4N$— are different or the same), or can proceed in a concurrent manner when the desired product is a symmetrically substituted s-triazine (that is, when $R_1$-, $R_2$- and $R_3R_4N$- are the same). Alternately, when two of the substituents are the same but different from the third group (for example, $R_3R_4N$- and $R_2$- are the same, but different from $R_1$-), the substitution steps may be a combination of a stepwise and concurrent reaction or may be conducted in a stepwise manner only.

The above reactions may be carried out in an inert solvent such as toluene or xylene for a period of time of from about 3 hours to 24 hours or more at temperatures ranging from about 25° C. to about 200° C. Lewis acids, such as $H^+$, $CF_3COOH$, $Sb(Hal)_5$ and alpha-pyridone may be used as catalyst in the above reactions or as the reaction solvent. Variation in the reaction time and temperature is dependent upon the structure of the amine reagent; less sterically hindered amines reacting most readily whereas sterically hindered amines react with more difficulty. When one or two molar equivalents of amine are used, then an acid scavenger such as sodium bicarbonate, soda ash, or a tertiary amine such as diisopropylethylamine should be employed to take up the hydrochloric acid produced in the reaction. In those cases where an excess of amine may be used, then an acid scavenger and/or an inert solvent may be dispensed with.

Other methods of preparation include reaction of melamine or N-substituted malamine with an olefin in the presence of alkali to provide an alkyl amino derivative, reaction of an amino-substituted-s-triazine with an aldehyde, ketone or cyclic ketone followed by reduction of the resultant product with such reducing agents as boiling formic acid, lithium aluminum hydride, or hydrogen in ethanol in the presence of platinum, palladium or other noble metal catalysts, trimeriazation of an appropriately substituted cyanamide in an inert solvent (such as methanol or ethanol) in the presence of alkali or hydrolysis of an N-acyl or N-hdyroxymethyl derivative of the compounds of this invention.

The preparation of symmetrical 2,4,6-tris(substituted-amino)-s-triazines may also be carried out by reacting cyanuric chloride with two equivalents of the amine in dilute aqueous sodium hydroxide or potassium hydroxide at the reflux temperature for a period of from about 3 hours to about 10 hours; the resultant 2,4-bis(substituted-amino)-6-chloro-s-triazine is then heated with excess amine as solvent and acid-scavenger or with a molar equivalent of amine in an inert solvent with a base such as diisopropylethylamine and/or a Lewis acid catalyst such as alpha-pyridone or antimony pentahalide. The preparation of these compounds can be accomplished by the trimerization of the cyanamide, especially the hindered t-alkyl cyanamides and the unsubstituted- and methyl-substituted-adamantyl cyanamides. These are trimerized as follows:

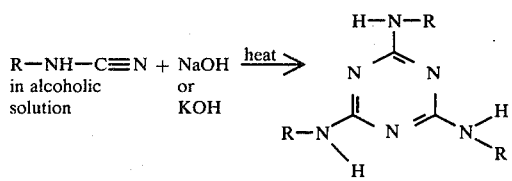

R—NH—C≡N + NaOH →(heat) [triazine structure]
in alcoholic   or
solution       KOH The products may be separated from the reaction mixtures and purified by standard techniques well known to those skilled in the art.

When $R_1$-, $R_2$- and $R_3NR_4$- are all different, the substitution of the amino groups at the 2-, 4- and 6- positions is carried out stepwise as indicated in the above reaction scheme employing equimolar amounts of amine and cyanuric chloride in the first step, an equimolar amount of another amine plus 2,4-dichloro-6-(substituted amino)-s-triazine in the second step, and an excess of amine and 2-chloro-4,6-bis(substituted amino)-s-triazine in the final step. The substitution may be carried out in any order. When two of the groups are to be the same, then two molecular equivalents of an amine are reacted with cyanuric chloride followed by treatment of the intermediate 2-chloro-4,6-bis(substituted-amino)-s-triazine with an excess of the other amine. Alternatively, when two of the groups are to be the same, one molecular equivalent of an amine is reacted with cyanuric chloride followed by treatment of the intermediate 2,4-dichloro-6-(substituted-amino)-s-triazine with an excess of the other amine. When $R_1$-, $R_2$- and $R_3R_4N$- are the same, then cyanuric chloride is treated with an excess of the appropriate amine to produce the corresponding 2,4,6-tris(substituted-amino)-s-triazine.

The invention will be described in greater detail in conjunction with the following specific examples.

EXAMPLE 1

Preparation of 2-chloro-4,6-bis(1,1,2,2-trimethylpropylamino)-s-triazine 6.7 g. (0.044 mole) of 2,3,3-trimethyl-2-butylamine hydrochloride and 3.4 g. (0.84 mole) NaOH in 20 ml. water are added to a stirred slurry of 3.6 g. (0.02 mole) cyanuric chloride in 150 ml. water. The reaction mixture is heated at reflux for 2½ hours, cooled and filtered to give the product, a white solid, m.p. 129°–131° C., 6.5 g.

EXAMPLE 2

Preparation of 2,4-bis(1,1,3,3-tetramethylbutylamino)-6-chloro-s-triazine 18.4 g. (0.10 mole) of cyanuric chloride is slurried in 100 ml. of water and the suspension cooled in an ice bath. Two drops of phenolphthalein solution are added, followed by addition of 32.3 g. (0.25 mole) 2,4,4-trimethyl-2-pentylamino whereupon an exothermic reaction ensues. The suspension is heated with stirring at reflux for a total of 17 hours. During the first half hour a solution of 8.0 g. (0.20 mole) sodium hydroxide in 40 ml. of water is added slowly so as to keep the reaction mixture slightly alkaline. The reaction mixture is cooled, and the aqueous solution decanted from the waxy solid. Acetone is added to the solid and the mixture is filtered to give 33.3 g. of product, m.p. 164°–168° C. Recrystallization from hot ethanol gives 27.5 g. of white needles, m.p. 165°–167° C.

EXAMPLE 3

Preparation of 3-{4,6-bis[(1,1,2,2-tetramethylpropyl)amino]-s-triazin-2-yl}-3-azabicyclo[3.2.2]nonane A 10.25 g. portion of 2-chloro-4,6-bis[(1,1,2,2-tetramethylpropyl)amino]-s-triazine and 7.65 g. of 3-azabicyclo[3.2.2]nonane in 50 ml. of diglyme is heated at reflux for 3 hours and then cooled, giving a pink solid. This solid is collected, washed with diglyme, suspended in 500 ml. of water, stirred, filtered and washed with water giving a pink solid. This solid is recrystallized from ethanol (charcoal being employed in decolorization) to give the desired product m.p. 282°–284° C.

EXAMPLE 4

Preparation of 3-[4,6-bis(1,1,3,3-tetramethylbutylamino)-s-triazin-2-yl]-3-azabicyclo[3.2.2]nonane A reaction mixture comprising 552 g. of cyanuric chloride, 969 g. of t-octylamine and 240 g. of sodium hydroxide in a 50% aqueous solution is refluxed for 2 hours, stirred at room temperature overnight and then dried at 60° C. The solid is recrystallized from 19 liters of 2B alcohol giving 1017 g. of 2-chloro-4,6-bis[(1,1,3,3-tetramethylbutyl)amino]-s-triazine.

A mixture of 11.1 g. of the product prepared as described above and 11.25 g. of 3-azabicyclo[3.2.2]nonane in 100 ml. of diglyme is refluxed for 3 hours, cooled and poured into water. The precipitated material is filtered giving the desired product. The product is recrystallized from 80% ethanol, m.p. 126°–127° C.

EXAMPLE 5

| Preparation of 50 mg. Tablets | | |
|---|---|---|
| Per Tablet | | Per 10,000 Tablets |
| 0.050 gm. | 2-(1-adamantylamino)-4,6-bis(1,1,2,2-tetramethyl-butylamino)-s-triazine | 500 gm. |
| 0.080 gm. | Lactose | 800 gm. |
| 0.010 gm. | Corn Starch (for mix) | 100 gm. |
| 0.008 gm. | Corn Starch (for paste) | 75 gm. |
| 0.148 gm. | | 1475 gm. |
| 0.002 gm. | Magnesium Stearate (1%) | 15 gm. |
| 0.150 gm. | | 1490 gm. |

The 2-(1-adamantylamino)-4,6-bis(1,1,2,2-tetramethylbutylamino)-s-triazine, lactose and corn starch (for mix) are blended together. The corn starch (for paste) is suspended in 600 ml. of water and heated with stirring to form a paste. This paste is then used to granulate the mixed powders. Additional water is used if necessary. The wet granules are passed through a No. 8 hand screen and dried at 120° F. The dry granules are then passed through a No. 16 screen. The mixture is lubricated with 1% magnesium stearate and compressed into tablets in a suitable tableting machine.

EXAMPLE 6

| Preparation of Oral Suspension | |
|---|---|
| Ingredient | Amount |
| 2-(2-adamantylamino)-4,6-bis(1,1,3-trimethylbutylamino)-s-triazine | 500 mg. |
| Sorbitol solution (70% N.F.) | 40 ml. |
| Sodium benzoate | 150 mg. |
| Saccharin | 10 mg. |
| Red dye | 10 mg. |
| Cherry flavor | 50 mg. |
| Distilled water gs. ad | 100 ml. |

The sorbitol solution is added to 40 ml. of distilled water and the 2-(2-adamantylamino)-4,6-bis(1,1,3-trimethylbutylamino)-s-triazine is suspended therein. The saccharin, sodium benzoate, flavor and dye are added and dissolved. The volume is adjusted to 100 ml. with distilled water. Each ml. of syrup contains 5 mg. of 2-(2-adamantylamino)-4,6-bis(1,1,3-trimethylbutylamino)-s-triazine.

EXAMPLE 7
Preparation of Parenteral Solution

In a solution of 700 ml. of propylene glycol and 200 ml. of water for injection is suspended 20.0 grams of $N^2$-(exo[2.2.1]norbornyl)-$N^4,N^6$-bis(1,1,4-trimethylpentyl)melamine with stirring. After suspension is complete the pH is adjusted to 5.5 with hydrochloric acid and the volume is made up to 1000 ml. with water for injection. The formulation is sterilized, filled into 5.0 ml. ampoules each containing 2.0 ml. (representing 40 mg. of drug) and sealed under nitrogen.

EXAMPLE 8

| Preparation of Topical Cream | |
|---|---|
| Ingredient | Amount |
| 2-(endo[2.2.1]norbornylamino)-4,6-bis(1,1,2,2-tetramethylbutylamino)-s-triazine | 1.0% |
| Ethoxylated stearyl alcohol | 10.0% |
| Benzyl alcohol | 0.9% |
| Isopropyl palmitate | 5.0% |
| Glycerin | 5.0% |
| Sorbitol solution (USP) | 5.0% |
| Lactic acid gs to pH 4.0-5.0 | |
| Water gs ad | 100.00% |

The ethoxylated stearyl alcohol and isopropyl palmitate are heated to liquifying temperature. About 95% of the total volume of water is placed in a separate container followed by the glycerin and sorbitol solution. This aqueous mixture is brought to a boil and then cooled to 60°-75° C. The 2-(endo[2.2.1]norbornylamino)-4,6-bis(1,1,2,2-tetramethylbutylamino)-s-triazine adjusted to 4.0-5.0 with lactic acid. The batch is cooled with minimum agitation until the cream sets in its final form.

EXAMPLE 9

| Preparation of Intra-articular Product | |
|---|---|
| Ingredient | Amount |
| 2-(3-azabicyclo[3.2.2]nonyl)-4,6-bis(1,1,3,3-tetramethylbutylamino)-s-triazine | 2-20 mg. |
| NaCl (physiological saline) | 0.9% |
| Benzyl alcohol N.F. | 0.9% |
| Sodium carboxymethylcellulose | 1.5% |

| -continued | |
|---|---|
| Preparation of Intra-articular Product | |
| Ingredient | Amount |
| pH adjusted to 5.0-7.5 | |
| Water for injection gs ad | 100% |

EXAMPLE 10

| Preparation of Injectable Depo Suspension | |
|---|---|
| Ingredient | % W/V |
| $N^2$-(1-adamantyl)-$N^4$,$N^6$-bis(1,1,2,2-tetramethylbutyl)melamine | 0.50-5 |
| Polysorbate 80 USP | 0.2 |
| Polyethylene glycol 4000 USP | 3.0 |
| Sodium chloride USP | 0.8 |
| Benzyl alcohol N.F. | 0.9 |
| HCL to pH 6-8 | gs |
| Water for injection gs ad | 100.0 |

EXAMPLE 11
Preparation of 3,3'-(6-chloro-s-triazine-2,4-diyl)bis-3-azabicyclo[3.2.2]nonane Eighty grams (0.43 mole) of cyanuric chloride is dissolved in 800 ml. of acetone, cooled to less than 10° C. and then one liter of water is added followed by 120 g. (0.96 mole) of 3-azabicyclo[3.2.2]nonane. After 2 hours the reaction is allowed to warm to room temperature and after a further 2 hours 35 g. (0.87 mole) of NaOH in 200 ml. of water is added over 2 hours. The reaction is then stirred for one hour and is then heated to reflux for a further one hour. Dilution with 2 l. of water gives a white precipitate which is filtered off and washed with water. The precipitate is then dissolved in one liter of chloroform and the aqueous solution separated. The aqueous solution is extracted with chloroform, the combined chloroform extracts washed with water, dried over magnesium sulfate and filtered through Magnesol ®. The Magnesol ® is then washed with one liter of chloroform, the solvent removed in vacuo, and the residue recrystallized from dichloromethane-hexanes giving 120 g. of colorless prisms, m.p. 195°-200° C.

EXAMPLE 12
Preparation of 3,3'-(6-butylamino-s-triazin-2,4-diyl)bis-3-azabicyclo[3.2.2]nonane Nine grams (0.025 mole) of 3,3'-(6-chloro-s-triazine-2,4-diyl)bis-3-azabicyclo[3.2.2]nonane and 9.7 g. (0.13 mole) n-butylamine is placed in a glass liner in a bomb and then heated in an oil bath maintained at 160°-180° C. for 16 hours. After cooling, the contents of the bomb are rinsed with chloroform and water into a flask and 50 ml. of 10 N NaOH is added. The solution is then evaporated in vacuo and the aqueous solution remaining is extracted with chloroform. The combined chloroform extracts are washed with water, dried over magnesium sulfate, filtered through Magnesol ® and the Magnesol ® washed with chloroform. Removal of solvent in vacuo, column chromatography on silica gel and recrystallization of the pure fractions containing the major component from n-heptane gives 4.9 g. of colorless prisms, m.p. 101°-103° C.

EXAMPLE 13

Preparation of
3-(4,6-dichloro-s-triazin-yl)-3-azabicyclo[3.2.2]nonane

Two hundred and eighty grams (1.5 mole) of cyanuric chloride is dissolved in 1.4 l. of acetone, then 1.8 l. of water is added and the mixture cooled to $-10°$ C. using a dry-ice/acetone bath. 130 g. (1.0 mole) of 3-azabicyclo[3.2.2]nonane slurried in 200 ml. of acetone is then added all at once and the reaction is allowed to stir at $-10°$ C. for 15 minutes. 100 ml. of 10 N NaOH is then added all at once giving rise to a small exotherm. After cooling to $-10°$ C. using the dry-ice/acetone bath, the reaction mixture is stirred without further cooling for 3.8 hours allowing the temperature to rise to about 20° C. Two liters of water is then added, the precipitate filtered off and then washed with water. The precipitate is then dissolved in chloroform, excess water separated, the chloroform solution dried over magnesium sulfate and filtered through Magnesol®. The Magnesol® is then washed with chloroform, solvent removed in vacuo and recrystallized from dichloromethane-hexanes giving 170 g. of needles, m.p. 153°–154° C.

EXAMPLE 14

Preparation of
3-[4,6-bis(tert-butylamino)-s-triazin-2-yl]-3-azabicyclo[3.2.2]nonane 3-(4,6-Dichloro-s-triazin-2-yl)-3-azabicyclo[3.2.2]nonane (8.2 g.; 0.03 mole) and 25 ml. (0.24 mole) of t-butylamine is placed in a glass liner in a bomb and then heated in an oil bath maintained at 160°–180° C. for 16 hours. After cooling, the contents of the bomb are rinsed with chloroform and water into a flask and 50 ml. of 10 N NaOH is added. The solution is then evaporated in vacuo and the aqueous solution remaining is extracted with chloroform. The combined chloroform extracts are washed with water, dried over magnesium sulfate, filtered through Magnesol® and the Magnesol® washed with chloroform. Removal of solvent in vacuo, column chromatography on silica gel and recrystallization of the pure fractions containing the more polar component from n-heptane gives 4.8 g. of fine colorless crystals, m.p. 217°–222° C.

EXAMPLE 15

Preparation of
3-[4-chloro-6-(1,1,3,3-tetramethylbutylamino)-s-triazin-2-yl]-3-azabicyclo[3.2.2]nonane Thirty grams (0.11 mole) of 3-(4,6-dichloro-s-triazin-2-yl)-3-azabicyclo[3.2.2]nonane is dissolved in 300 ml. of acetone and then 370 ml. of water is added followed by 20 g. (0.15 mole) of tert-octylamine. After stirring for 10 minutes, 4.4 g. (0.11 mole) of NaOH in 30 ml. of water is added over 20 minutes. The reaction is then heated to reflux for 19 hours. After cooling to room temperature, one liter of water is added, stirred for one hour and the white precipitate filtered off. The precipitate is washed with water, dried overnight, dissolved in dichloromethane and filtered through Magnesol®. The Magnesol® is then washed with dichloromethane, solvent removed in vacuo and recrystallized from dichloromethane-hexanes giving 20 g. of colorless crystals, m.p. 159°–162.5° C.

EXAMPLE 16

Preparation of
3-[4-p-fluoroanilino-6-(1,1,3,3-tetramethylbutylamino)-s-triazin-2-yl]-3-azabicyclo[3.2.2]nonane Eight grams (0.022 mole) of 3-[4-chloro-6-(1,1,3,3-tetramethylbutylamino)-s-triazin-2-yl]-3-azabicyclo[3.2.2]nonane and 21 ml. (0.22 mole) of p-fluoroaniline is placed in a glass liner in a bomb and then heated in an oil bath maintained at 190°–205° C. for about 40 hours. After cooling, the indigo contents of the bomb are rinsed with chloroform and water into a flask and 50 ml. of 10 N NaOH is added. The solution is then evaporated in vacuo and the aqueous solution remaining is extracted with chloroform. The combined chloroform extracts are washed with water, dried over magnesium sulfate, filtered through Magnesol® and the Magnesol® washed with chloroform. Removal of solvent in vacuo, addition of toluene and re-evaporation in vacuo several times gives an orange solid which on slurrying with acetone gives white crystals. Recrystallization from acetone gives 7.1 g. of colorless crystals m.p. 173.5°–174.5° C.

EXAMPLE 17

Preparation of
3-[4-tert-butyl-6-(1,1,3,3-tetramethylbutylamino)-s-triazin-2-yl]-3-azabicyclo[3.2.2]nonane Eight grams (0.022 mole) of 3-[4-chloro-6-(1,1,3,3-tetramethylbutylamino)-s-triazin-2-yl]-3-azabicyclo[3.2.2]nonane and 23 ml. (0.22 mole) of t-butylamine is placed in a glass liner in a bomb and then heated in an oil bath maintained at 185°–200° C. for about 40 hours. After cooling, the contents of the bomb are rinsed with chloroform and water into a flask and 50 ml. of 10 N NaOH is added. The solution is then evaporated in vacuo and the aqueous solution remaining is extracted with chloroform. The combined chloroform extracts are washed with water, dried over magnesium sulfate, filtered through Magnesol® and the Magnesol® washed with chloroform. Removal of solvent in vacuo and recrystallization from acetone gives 5.8 g. of colorless crystals, m.p. 163.5°–167.5° C.

EXAMPLE 18

Preparation of
3-[4-(1,1,3,3-tetramethylbutylamino)-6-[(1,1,2,2-tetramethylpropyl)amino]-s-triazin-2-yl]-3-azabicyclo[3.2.2]nonane Eight grams (0.022 mole) of 3-[4-chloro-6-(1,1,3,3-tetramethylbutylamino)-s-triazin-2-yl]-3-azabicyclo[3.2.2]nonane and 20 g. (0.17 mole) of t-heptylamine is placed in a glass liner in a bomb and then heated in an oil bath maintained at 220° C. for 88 hours. After cooling, the contents of the bomb are rinsed with chloroform and water into a flask and 50 ml. of 10 N NaOH is added. The solution is then evaporated in vacuo and the aqueous solution remaining is extracted with chloroform. The combined chloroform extracts are washed with water, dried over magnesium sulfate, filtered through Magnesol® and the Magnesol® washed with chloroform. Removal of solvent in vacuo, addition of toluene and re-evaporation in vacuo several times followed by recrystallization from acetone gives 3.9 g. of colorless crystals, m.p. 98°–102° C.

EXAMPLE 19

Preparation of 2-chloro-4,6-bis[(1,1,2,2-tetramethylpropyl)amino]-s-triazine

Twenty grams (0.5 mole) of NaOH in 220 ml. of water is added all at once to a stirred suspension of 44 g. (0.24 mole) of cyanuric chloride and 60 g. (0.46 mole) of t-heptylamine in one liter of water. The reaction is then heated to reflux and after 3 hours is allowed to cool to room temperature. The precipitate is filtered off and air dried in the funnel overnight to give 76 g. of a white powder, m.p. 131°–133.5° C.

EXAMPLE 20

Preparation of 2-(1,8,8-trimethyl-3-azabicyclo[3.2.1]octyl)-4,6-bis(1,1,2,2-tetramethylpropylamino)-s-triazine Seven grams (0.02 mole) of 2-chloro-4,6-bis[(1,1,2,2-tetramethylpropyl)amino]-s-triazine, 31 g. (0.2 mole) of 1,8,8-trimethyl-3-azabicyclo[3.2.1]octane, 7.1 ml. (0.04 mole) of N,N-diisopropylethylamine and xylene are refluxed under an argon atmosphere for 22 hours. After cooling, the reaction is diluted with ethyl acetate and water. The mixture is then washed with water, the organic phase dried over magnesium sulfate, filtered through diatomaceous earth and evaporated in vacuo. Addition of toluene and re-evaporation in vacuo several times gives a solid. This solid is then dissolved in dichloromethane, filtered through Magnesol ® and the Magnesol ® washed with dichloromethane. Evaporation of the solvent and purification by column chromatography gives 2-(1,8,8-trimethyl-3-azabicyclo[3.2.1]octyl)-4,6-bis(1,1,2,2-tetramethylpropylamino)-s-triazine.

EXAMPLE 21

Preparation of $N^2$-1-adamantyl-$N^4$,$N^6$-bis(1,1,2,2-tetramethylpropyl)-melamine Seven grams (0.02 mole) of 2-chloro-4,6-bis[(1,1,2,2-tetramethylpropyl)amino]-s-triazine is ground up in a mortar and 24 g. (0.16 mole) of 1-adamentylamine is intimately mixed, placed in a glass liner in a bomb and then heated in an oil bath maintained at 210°–220° C. for 20 hours. After cooling, the contents of the bomb are rinsed with chloroform and water into a flask and 50 ml. of 10 N NaOH is added. The solution is then evaporated in vacuo and the aqueous solution remaining is extracted with chloroform. The combined chloroform extracts are washed with water, dried over magnesium sulfate, filtered through Magnesol ® and the Magnesol ® washed with chloroform. Removal of solvent in vacuo, addition of toluene and re-evaporation in vacuo several times gives 28 g. of solid. Column chromatography of this solid on silica gel and recrystallization of the pure fractions containing the least polar component from acetone give 7.9 g. of colorless crystals m.p. 215.5°–218° C.

EXAMPLE 22

Preparation of $N^2$-2-adamantyl-$N^4$,$N^6$-bis(1,1,2,2-tetramethylpropyl)-melamine Seven grams (0.02 mole) of 2-chloro-4,6-bis[(1,1,2,2-tetramethylpropyl)amino]-s-triazine, 7.7 g. (0.041 mole) of 2-adamentylamine hydrochloride, 11 ml. (0.061 mole) of N,N-diisopropylethylamine and xylene are refluxed under an argon atmosphere for 20 hours. After cooling, the reaction is diluted with ethyl acetate and water. The mixture is then washed with water, the organic phase dried over magnesium sulphate, filtered through diatomaceous earth and evaporated in vacuo to give a pale yellow solid, 11 g. This solid is then dissolved in dichloromethane and filtered through Magnesol ®. Evaporation of the solvent in vacuo and recrystallization from n-heptane gives 3.0 g. of colorless crystals, m.p. 244°–249° C.

EXAMPLE 23

Preparation of exo-$N^2$-2-norbornyl-$N^4$,$N^6$-bis[(1,1,2,2-tetramethylpropyl)amino]-melamine Seven grams (0.02 mole) of 2-chloro-4,6-bis[(1,1,2,2-tetramethylpropyl)amino]-s-triazine and 24 ml. (0.2 mole) of exo-2-norbornylamine is placed in a glass liner in a bomb and then heated in an oil bath maintained at 185°–195° C. for 19–20 hours. After cooling, the contents of the bomb are rinsed with chloroform and water into a flask and 50 ml. of 10 N NaOH is added. The solution is then evaporated in vacuo and the aqueous solution remaining is extracted with chloroform. The combined chloroform extracts are washed with water, dried over magnesium sulfate, filtered through Magnesol ® and the Magnesol ® washed with chloroform. Removal of solvent in vacuo and recrystallization from acetone gives 7 g. of colorless crystals, m.p. 159°–163° C.

EXAMPLE 24

Preparation of 2-(3-azabicyclo[3.3.1]nonyl)-4,6-bis(1,1,2,2-tetramethylpropylamino)-s-triazine By replacing the 1,8,8-trimethyl-3-azabicyclo[3.2.1]octane employed in Example 20 with an equimolar amount of 3-azabicyclo[3.3.1]nonane, there is obtained the corresponding 2-(3-azabicyclo[3.3.1]nonyl)-4,6-bis(1,1,2,2-tetramethylpropylamino)-s-triazine in equally good yield.

EXAMPLE 25

Preparation of 2-(9-azabicyclo[3.3.1]nonyl)-4,6-bis(1,1,2,2-tetramethylpropylamino)-s-triazine The general procedure of Example 20 is repeated but replacing the 1,8,8-trimethyl-3-azabicyclo[3.2.1]octane employed in that example with an equivalent amount of 9-azabicyclo[3.3.1]nonane whereby there is obtained the 2-(9-azabicyclo[3.3.1]nonyl)-4,6-bis(1,1,2,2-tetramethylpropylamino)-s-triazine as colorless crystals.

EXAMPLE 26

Preparation of 2-(3-azabicyclo[3.2.1]-octyl)-4-(3-azabicyclo[3.2.2-]nonyl)-6-(1,1,3,3-tetramethylbutylamino)-s-triazine In the manner described in Example 16, reaction of 3-[4-chloro-6-(1,1,3,3-tetramethylbutylamino)-s-triazin-2-yl]-3-azabicyclo[3.2.2]nonane with 3-azabicyclo[3.2.1]octane provides the title compound after purification by column chromatography.

EXAMPLE 27

Preparation of 2,4,6-tris(2-azabicyclo[3.2.2]nonyl)-s-triazine

Treatment of cyanuric chloride with a three-fold molar excess of 2-azabicyclo[3.2.2]nonane in diglyme as solvent at the reflux temperature for three hours provides the title compound as colorless crystals.

We claim:

1. A compound of the formula:

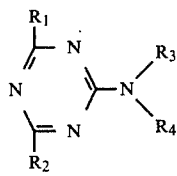

and the pharmaceutically acceptable acid-addition and quaternary ammonium salts thereof wherein $R_1$ is alkylamino having from 4 to 8 carbon atoms, inclusive, 1-adamantylamino, 2-adamantylamino, exo[2.2.1]norbornylamino, endo[2.2.1]norbornylamino, 3-azabicyclo[3.2.1]octyl, 1,8,8-trimethyl-3-azabicyclo[3.2.1]octyl, 3-azabicyclo[3.3.1]nonyl, 9-azabicyclo[3.3.1]nonyl, 2-azabicyclo[3.2.2]nonyl, 3-azabicyclo[3.2.2]nonyl or endo-3- hydroxy-8-azabicyclo[3.2.1]oct-8-yl; $R_2$ is 3-azabicyclo[3.2.1]octyl, 1,8,8-trimethyl-3-azabicyclo[3.2.1]octyl, 3-azabicyclo[3.3.1]nonyl, 9-azabicyclo[3.3.1]nonyl, 2-azabicyclo[3.2.2]nonyl, 3-azabicyclo[3.2.2.]nonyl or endo-3-hydroxy-8-azabicyclo[3.2.1]oct-8-yl; $R_3$ is hydrogen or alkyl having up to 4 carbon atoms; $R_4$ is 2-(2-pyridyl)ethyl, alkyl having from 4 to 8 carbon atoms, inclusive, phenyl, monohalo(F, Cl, Br)phenyl, 1-adamantyl, 2-adamantyl, exo[2.2.1]norbornyl, endo[2.2.1]norbornyl or a monovalent moiety of the formula:

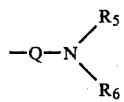

wherein Q is a divalent moiety of the formulae:

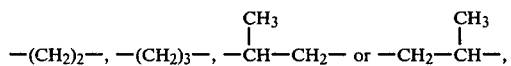

$R_5$ is alkyl having up to 4 carbon atoms, $R_6$ is alkyl having up to 4 carbon atoms, and $R_5$ and $R_6$ taken together with their associated N(itrogen) is piperidino, morpholino, pyrrolidino or thiomorpholino with the proviso that when $R_4$ is alkyl, adamantyl or norbornyl then $R_3$ must be hydrogen; and $R_3$ and $R_4$ taken together with their associated N(itrogen) is 3-azabicyclo[3.2.1]octyl, 1,8,8-trimethyl-3-azabicyclo[3.2.1]octyl, 3-azabicyclo[3.3.1]nonyl, 9-azabicyclo[3.3.1]nonyl, 2-azabicyclo[3.2.2]nonyl, 3-azabicyclo[3.2.2]nonyl, endo-3-hydroxy-8-azabicyclo[3.2.1]oct-8-yl, pyrrolidino, piperidino, hexamethyleneimino, heptamethyleneimino or a monovalent moiety of the formula:

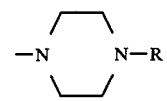

wherein R is hydrogen, alkyl having up to 4 carbon atoms, phenyl, p-methoxyphenyl or carboalkoxy having up to 4 carbon atoms.

2. The compound according to claim 1 wherein $R_1$, $R_2$ and $NR_3R_4$ are all 3-azabicyclo[3.2.2]nonyl; 2,4,6-tris(3-azabicyclo[3.2.2]nonyl)-s-triazine.

3. The compound according to claim 1 wherein $R_1$ is (1,1,2,2-tetramethylpropyl)amino, $R_2$ is 3-azabicyclo[3.2.2]nonyl, $R_3$ is hydrogen and $R_4$ is 1,1,2,2-tetramethylpropyl; 3-azabicyclo[3.2.2]nonane, 3-{4,6-bis[(1,1,2,2-tetramethylpropyl)amino]-s-triazin-2-yl}.

4. The compound according to claim 1 wherein $R_1$ is (1,1,3,3-tetramethylbutyl)amino, $R_2$ is 3-azabicyclo[3.2.2]nonyl, $R_3$ is hydrogen and $R_4$ is 1,1,3,3-tetramethylbutyl; 3-azabicyclo[3.2.2]nonane, 3-[4,6-bis(1,1,3,3-tetramethylbutylamino)-s-triazin-2-yl].

5. The compound according to claim 1, wherein $R_1$ and $R_2$ are 3-azabicyclo[3.2.2]nonyl, $R_3$ is hydrogen and $R_4$ is n-butyl; 3,3'-(6-butylamino-s-triazin-2,4-diyl)bis-3-azabicyclo[3.2.2]nonane.

6. The compound according to claim 1 wherein $R_1$ is t-butylamino, $R_2$ is 3-azabicyclo[3.2.2]nonyl, $R_3$ is hydrogen and $R_4$ is t-butyl; 3-[4,6-bis(tert-butylamino)-s-triazin-2-yl]-3-azabicyclo[3.2.2]nonane.

7. The compound according to claim 1 wherein $R_1$ is t-butylamino, $R_2$ is 3-azabicyclo[3.2.2]nonyl, $R_3$ is hydrogen and $R_4$ is 1,1,3,3-tetramethylbutyl; 3-[4-tert-butyl-6-(1,1,3,3-tetramethylbutylamino)-s-triazin-2-yl]-3-azabicyclo[3.2.2]nonane.

8. The compound according to claim 1 wherein $R_1$ is (1,1,2,2-tetramethylpropyl)amino, $R_2$ is 3-azabicyclo[3.2.2]nonyl, $R_3$ is hydrogen and $R_4$ is 1,1,3,3-tetramethylbutyl; 3-[4-(1,1,3,3-tetramethylbutylamino)-6-[(1,1,2,2-tetramethylpropyl)amino]-s-triazin-2-yl]-3-azabicyclo[3.2.2]nonane.

9. The compound according to claim 1 wherein $R_1$ and $R_2$ are both 3-azabicyclo[3.2.2]nonyl, $R_3$ is hydrogen and $R_4$ is 1,1,2,2-tetramethylpropyl; 3-azabicyclo[3.2.2]nonane, 3,3'-[6-(1,1,2,2-tetramethylpropyl)-s-triazine-2,4-diyl]bis-.

10. The compound according to claim 1 wherein $R_1$ is exo[2.2.1]norbornylamino, $R_2$ is 3-azabicyclo[3.3.2]nonyl, $R_3$ is hydrogen and $R_4$ is 1,1,2,2-tetramethylpropyl; 3-azabicyclo[3.2.2]nonane, 3-[4-(2-norbornylamino)-[(1,1,2,2-tetramethylpropyl)amino]-s-triazin-2-yl]-,exo.

11. The compound according to claim 1 wherein $R_1$ is tert-butylamino, $R_2$ is 3-azabicyclo[3.2.2]nonyl, $R_3$ is hydrogen and $R_4$ is 1,1,2,2-tetramethylpropyl; 3-azabicyclo[3.2.2]nonane, 3-[4-tert-butylamino-6-[(1,1,2,2-tetramethylpropyl)amino]-s-triazin-2-yl-.

* * * * *